United States Patent [19]

Baker et al.

[11] Patent Number: 5,543,132
[45] Date of Patent: Aug. 6, 1996

[54] X-RAY CONTRAST COMPOSITIONS CONTAINING A BARIUM SALT AND A CELLULOSE DERIVATIVE

[75] Inventors: Edward J. Baker, Northumberland, England; Robert W. Lee, Gilbertsville, Pa.; John L. Toner, Downingtown, Pa.; Carl R. Illig, Phoenixville, Pa.

[73] Assignee: Sterling Winthrop Inc., New York, N.Y.

[21] Appl. No.: 227,422

[22] Filed: Apr. 14, 1994

[51] Int. Cl.⁶ ................................... A61K 49/04
[52] U.S. Cl. .............. 424/9.411; 424/709; 514/57; 514/558; 514/941; 514/942
[58] Field of Search ............. 424/4, 709, 9.411; 514/54, 57, 941, 942, 558

[56] References Cited

U.S. PATENT DOCUMENTS

| | | | |
|---|---|---|---|
| 2,659,690 | 6/1950 | Slaybaugh | 167/95 |
| 2,680,089 | 6/1954 | Lowy | 167/95 |
| 2,832,722 | 8/1958 | Singher | 167/95 |
| 3,192,118 | 6/1965 | Battista et al. | 167/95 |
| 4,038,379 | 7/1977 | Elinov et al. | 424/4 |
| 4,069,306 | 1/1978 | Rothman | 424/4 |
| 4,120,946 | 10/1978 | Quemille et al. | 424/4 |
| 4,588,574 | 5/1986 | Felder et al. | 423/554 |
| 5,019,370 | 5/1991 | Jay et al. | 424/4 |
| 5,318,768 | 6/1994 | Illig et al. | 424/5 |
| 5,352,434 | 10/1994 | Illig et al. | 424/4 |

FOREIGN PATENT DOCUMENTS 55-127322  10/1980  Japan.

OTHER PUBLICATIONS

Wang et al, Yaoxne Xuebao, vol. 16, No. 8:610–617 (1981).
James et al, Pharm. Acta. Helvetiae, 47, 244–256 (1972).

*Primary Examiner*—Gary E. Hollinden
*Attorney, Agent, or Firm*—Fish & Richardson PC

[57] ABSTRACT

Disclosed are x-ray contrast compositions for oral or retrograde examination of the gastrointestinal tract comprising a barium salt in a pharmaceutically acceptable carrier comprising a cellulose derivative; and methods for their use in diagnostic radiology of the gastrointestinal tract.

16 Claims, No Drawings

X-RAY CONTRAST COMPOSITIONS CONTAINING A BARIUM SALT AND A CELLULOSE DERIVATIVE

BACKGROUND OF THE INVENTION

1. Field of the Invention

This invention relates to an x-ray contrast composition for oral or retrograde administration to a mammal comprising a barium salt as the contrast producing agent in a pharmaceutically acceptable carrier comprising a cellulose derivative.

2. Reported Developments

Roentgenographic examination utilizing x-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate x-ray radiation. D. P. Swanson et al in "Pharmaceuticals In Medical Imaging", 1990, MacMillan Publishing Company, provides an excellent background in medical imaging utilizing contrast agents and compositions therewith.

The desiderata for an ideal GI contrast agent includes: good toxicological profile; the ability to fill the entire bowel/lumen and evenly coat the gut mucosa so that the presence of the bowel is detectable when the lumen is not distended; palatability and nonirritation to the intestinal mucosa; and passing through the GI tract without producing artifacts or stimulating vigorous intestinal peristalsis.

The most widely used contrast agents for the visualization of the GI tract is barium sulfate administered as a suspension orally or rectally as an enema. (See for example, U.S. Pat. Nos. 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids, it lacks homogeneity which can result in poor x-ray images. In the colon, when administered as an enema, it flocculates and forms irregular clumps with fecal matter. The prior art considers as a serious problem the difficulty in achieving uniform adherence to, and coating of, the mucosa of the GI tract by the water insoluble barium sulfate to provide high quality x-ray photographs. As a result of inadequate adherence to, and non-uniform coating of the mucosa, the x-ray results are often inferior, misleading to the practitioner and the imaging process must be repeated. It has also been observed that the barium sulfate, and other solid inorganic particulate radiopaque agents tend to settle out in the patient after evacuation but before and during x-ray imaging, which again deleteriously affects the quality of the x-ray pictures.

These drawbacks were addressed by many investigators and their efforts resulted in great improvements over the years. The drawbacks of uneven coating of the mucosa by an x-ray contrast composition and insufficient adherence to the mucosa proved to be rather difficult to solve. To that end, the use of certain polymer additives were proposed as illustrated hereunder.

U.S. Pat. No. 4,069,306 discloses an x-ray contrast preparation which is said to adhere to the walls of body cavities. The preparation comprises a finely divided water-insoluble inorganic x-ray contrast agent and minute particles of a hydrophilic polymer which is insoluble in water but is water-swellable. The body cavity is supplied with such preparation suspended in water. The x-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to x-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intraarterially.

Japanese Patent Application No. 55-127322 discloses x-ray contrast compositions containing barium sulfate and a polymeric substance selected from carboxymethyl cellulose salts, propylene glycol alginate, cellulose sulfate polyacrylate, pectin and tragacanth gum. The polymeric substance is used to increase the viscosity of the compositions.

While these polymeric materials enhance attachment of the contrast agent used therewith to the walls of organs for better visualization thereof, there is still a need for an improved x-ray imaging medium that uniformly coats the soft tissues subjected to diagnostic x-ray examination.

We have now discovered that good adherence to, and uniform coating of the mucosa of the intestine can be obtained by a barium salt in combination with a cellulose derivative.

SUMMARY OF THE INVENTION

It is the object of the present invention to provide compositions for coating the gastrointestinal tract of mammals to form an effective radiopaque coating thereon by which diagnostic examination of the GI tract may be accomplished.

The object of the present invention is achieved by a composition comprising: a barium salt as x-ray contrast agent in a pharmaceutically acceptable vehicle comprising a cellulose derivative.

The preferred x-ray contrast agent utilized in the present invention is barium sulfate which is a white, radiopaque, crystalline powder that is essentially insoluble in water. It is commercially available in the particle size range of 0.001 to 0.1 micron diameter. However, good results are obtainable with other finely-divided, inorganic, essentially water-insoluble salts of barium including barium hexaboride, barium chromite, barium fluogallate, barium tri-ortho phosphate, barium metasilicate, barium titanate, barium zirconate and zirconium oxide. The compositions of the present invention contain from about 5% w/w to about 95% w/w of the barium salt. The compositions may be in the form of dispersions, colloids or suspensoids, however, we prefer to use colloids as the preferred embodiment.

The cellulose derivative utilized in the present invention includes methylcellulose, carboxymethylcellulose, sodium carboxymethylcellulose, hydroxyethyl methylcellulose, hydroxypropyl methylcellulose; and microcrystalline cellulose having an average particle size of from 0.01 to 100 µ, more preferably of from 0.05 to 10 µ, and most preferably of from 0.1 to 1 µ.

The barium salt and the cellulose derivative are formulated for administration using physiologically acceptable carriers or excipients in a manner within the skill of the art. The barium salt and the cellulose derivative with the addition of pharmaceutically acceptable aids (such as surfactants and emulsifiers) and excipients are suspended in an aqueous medium resulting in a dispersion, suspension or emulsion.

A method for diagnostic imaging of the GI tract for use in medical procedures in accordance with this invention comprises orally or rectally administering to the mammalian patient in need of an x-ray examination, an effective contrast producing amount of a composition of the present invention. After administration at least a portion of the GI tract containing the administered composition is exposed to x-rays to produce an x-ray image pattern corresponding to the presence of the contrast agent, then the x-ray image is visualized and interpreted using techniques known in the art.

DETAILED DESCRIPTION OF THE INVENTION

Starting materials, reagents and solvents can be obtained from chemical suppliers, such as Aldrich, Baker and Eastman Chemical Companies; alternatively, they may be prepared by techniques known in the prior art.

Compositions of the Present Invention

The barium salts may be formulated for administration using physiologically acceptable carriers or excipients in a manner within the skill of the art. The barium salts with the addition of pharmaceutically acceptable aids (such as surfactants and emulsifiers) and excipients may be suspended in an aqueous medium resulting in a dispersion, suspension or emulsion.

Compositions of the present invention comprise the following pharmaceutically acceptable components based on % w/v:

| Ingredients | Broad Range | Preferred Range |
|---|---|---|
| Barium Salt (w/v) | 5–95 | 40–70 |
| Cellulose derivative (% w/v) | 0.1–10 | 0.2–1 |
| Oily Vehicle (% w/v) | 0.1–55 | 7–15 |
| Surfactant (% w/v) | 0.1–20 | 3–7 |
| Viscosity modifying excipients (% w/v) | 0.001–15 | 0.05–1 |
| Water — q.s. to 100% by volume | | |

To stabilize particulates in the compositions of the present invention electrolytes may be used in the range of from about 0.01 to about 10% w/v based on the total composition. Such electrolytes include sodium chloride, potassium chloride, citric acid and salts thereof, phosphoric acid and salts thereof and aluminum chloride.

The preferred cellulose derivative utilized in the present invention is AVICEL® RC-591, which is a mixture of about 89 parts microcrystalline cellulose and about 11 parts of sodium carboxymethylcellulose.

In further reference to the barium salts used in the compositions of the present invention the following should be noted.

The barium salts present in concentrations lower than the above-stated minimum in formulations does not provide good quality x-ray or CT images, while concentrations above the maximum concentration render the GI tract too radiopaque and do not allow sufficient delineation of the GI tract.

Depending on the form and amount of cellulose derivative used, additions of viscosity modifying agents may not be necessary; at higher levels than about 15% w/v the viscosity is too high and gels will tend to form.

The following formulation examples will further illustrate the invention.

EXAMPLE 1

| Components | Amounts in % w/v |
|---|---|
| Barium Sulfate | 17.50 |
| Polysorbate 80 (Tween 80) | 3.37 |
| Sorbitan Mono-oleate (Span 80) | 1.64 |
| AVICEL® RC-591 | 0.50 |
| q.s. with water to 100% by volume | |

EXAMPLE 2

| Components | Amounts in % w/v |
|---|---|
| Barium Hexaboride | 25.00 |
| Light Mineral Oil, NF | 9.50 |
| Polysorbate 80 (Tween 80) | 5.00 |
| AVICEL® RC-591 | 6.50 |
| q.s. with water to 100% by volume | |

EXAMPLE 3

| Components | Amounts in % w/v |
|---|---|
| Barium Chromite | 70.00 |
| Light Mineral Oil, NF | 5.00 |
| Polysorbate 20 (Tween 20) | 2.50 |
| Sorbitan Mono-laurate (Span 20) | 2.50 |
| AVICEL® RC-591 | 0.50 |
| q.s. with water to 100% by volume | |

EXAMPLE 4

| Components | Amounts in % w/v |
|---|---|
| Barium Metasilicate | 85.00 |
| Polysorbate 20 (Tween 20) | 2.50 |
| Sorbitan Mono-laurate (Span 20) | 2.50 |
| AVICEL® RC-591 | 0.75 |
| q.s. with water to 100% by volume | |

EXAMPLE 5

| Components | Amounts in % w/v |
|---|---|
| Barium Fluogallate | 50.00 |
| Mineral Oil NF | 10.00 |
| Polysorbate 80 (Tween 80) | 3.37 |
| Sorbitan Mono-oleate (Span 80) | 1.64 |
| AVICEL® RC-591 | 0.50 |
| q.s. with water to 100% by volume | |

EXAMPLE 6

| Components | Amounts in % w/v |
|---|---|
| Barium Tri-orthophosphate | 60.00 |
| Polysorbate 80 (Tween 80) | 5.00 |
| AVICEL ® RC-591 | 2.00 |
| q.s. with water to 100% by volume | |

As known by those skilled in the art, surfactants or emulsifiers can reduce the interfacial tension between two immiscible phases, i.e., oil-inaqueous medium. These agents can be used alone or in combination with other emulsifying agents and surfactants. For example, Dow Corning Medical Antifoam AF, which is a composition of 30% w/v polydimethylsiloxane (simethicone) and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The amount of such surfactants may be in the range of from 0.1 to 20% w/v of the aqueous formulations, although the amount, in general, is kept as low as possible, preferably in the range of 3 to 7% w/v. The surface active agents may be cationic, anionic, nonionic, zwitterionic or a mixture of two or more of these agents.

Suitable cationic surfactants include cetyl trimethyl ammonium bromide. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out the molecules act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less of an irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example, mono-esters formed by the reaction of fatty and resin adds, for example of about 8 to about 18 carbon atoms, with polyhydric alcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial adds, for example, mono- esters of ethylene oxide, such as fatty or resin acid esters of polyoxyethylene sorbitan and sorbitol, for example polyoxyethylene sorbitan. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamine and diethylamine amides of fatty acids having an acyl chain of from about 8 to about 18 carbon atoms.

The ethoxylated alkylphenol nonionic surface active agents include various polyethylene oxide condensates of alkylphenols, especially the condensation products of monoalkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include: sorbitan esters (sold under the trade name Span) having the formula:

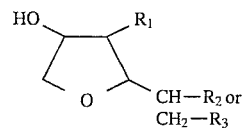

wherein $R_1=R_2=OH$, $R_3=R$ for sorbitan monoesters, $R_1=OH$, $R_2=R_3=R$ for sorbitan diesters, $R_1=R_2=R_3=R$ for sorbitan triesters, where $R =(C_{11}H_{23})$ COO for laurate, $(C_{17}H_{33})$ COO for oleate, $(C_{15}H_{31})$ COO for palmitate, $(C_{17}H_{35})$ COO for stearate.

Polyoxyethylene alkyl ethers (i.e. Brijs) having the formula:

$$CH_3(CH_2)_x(O-CH_2-CH_2)_yOH$$

where $(x +1)$ is the number of carbon atoms in the alkyl chain, typically:

| | |
|---|---|
| 12 lauryl | (dodecyl) |
| 14 myristyl | (tetradecyl) |
| 16 cetyl | (hexadecyl) |
| 18 stearyl | (octadecyl) | and y is the number of ethylene oxide groups in the hydrophilic chain, typically 10–60.

Polyoxyethylene sorbitan fatty acid esters (Polysorbates 20, 40, 60, 65, 80 & 85) sold under the trade names of Tweens, Crillers, Sodares and Monitans, having the formulas (1) and (2)

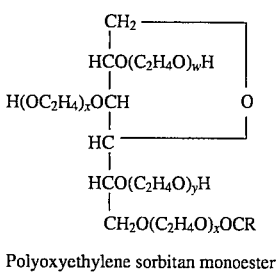

Polyoxyethylene sorbitan monoester

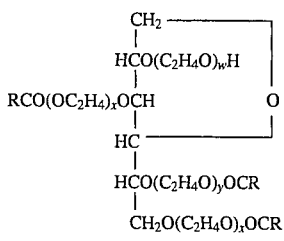

Polyoxyethylene sorbitan triester wherein w+x+y+z =20 (Polysorbate 20, 40, 60, 65, 80 and 85)

w+x+y+z =5 (Polysorbate 81)

w+x+y+z =4 (Polysorbate 21 and 61).

Polyethylene stearates, such as:

poly(oxy-1,2-ethanediyl),α-hydro-ω-hydroxyoctadecanoate;

polyethylene glycol monostearate; and poly(oxy-1,2-ethanediyl)-α-(1-oxooctadecyl)-ω-hydroxy-polyethylene glycol monostearate.

The compositions of the invention may be administered orally to the patient for radiological examination of the GI tract. The compositions of the invention may also be administered rectally in the form of enemas to a patient for radiologic examination of the colon.

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 0.8 to about 2.0 g iodine/kg body weight for regular x-ray visualization of the GI tract. For CT scanning, the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

The compositions of the present invention possess very good adherence to the walls of the gastrointestinal tract by forming an essentially uniform coating thereon.

The invention having been fully described, it will be apparent to one skilled in the art that changes and modifications can be made thereto without departing from the spirit and scope thereof.

What is claimed is:

1. An x-ray contrast composition for oral or retrograde examination of the gastrointestinal tract comprising:

(a) from about 5 to 95% w/v of a barium salt;

(b) from 0.1 to 10% w/v of a cellulose derivative comprising microcrystalline cellulose (c) from 0.1 to 55% w/v of an oily vehicle;

(d) from 0.1 to 20% w/v of a surfactant selected from the group consisting of nonionic, anionic, cationic and zwitterionic surfactants;

(e) from 0.001 to 15% w/v of a viscosity modifying excipient; and (f) water to make 100% by volume.

2. The x-ray contrast composition of claim 1 wherein said oily vehicle constitutes from 7 to 15% w/v of the composition.

3. The x-ray contrast composition of claim 1 wherein said surfactant constitutes from 3 to 7% of the composition.

4. The x-ray contrast composition of claim 1 wherein said microcrystalline cellulose has an average particle size of from 0.01 to 100μ.

5. The x-ray contrast composition of claim 4 wherein said microcrystalline cellulose is about 89 parts microcrystalline cellulose and about 11 parts of sodium carboxymethylcellulose.

6. The x-ray contrast composition of claim 1 wherein said nonionic surface active agent is selected from the group consisting of carboxylic esters, carboxylic amides, ethoxylated alklyphenols and ethoxylated aliphatic alcohols.

7. The x-ray contrast composition of claim 1 wherein said surfactant is sorbitan ester having the formula:

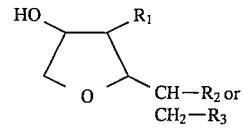

wherein $R_1=R_2=OH$, $R_3=R$ for sorbitan monoesters, $R_1=OH$, $R_2=R_3=R$ for sorbitan diesters, $R_1=R_2=R_3=R$ for sorbitan triesters, where $R=(C_{11}H_{23})$ COO for laurate, $(C_{17}H_{33})$ COO for oleate, $(C_{15}H_{31})$ COO for palmitate, $(C_{17}H_{35})$ COO for stearate.

8. The x-ray contrast composition of claim 1 wherein said surface active agent is polyoxyethylene alkyl ether having the formula:

$$CH_3(CH_2)_x(O-CH_2-CH_2)_yOH$$

where (x+1) is the number of carbon atoms in the alkyl chain, and y is the number of ethylene oxide groups in the hydrophilic chain from about 10 to about 60.

9. The x-ray contrast composition of claim 1 wherein said surfactant is polyoxyethylene sorbitan fatty acid ester of the formulas (1) and (2)

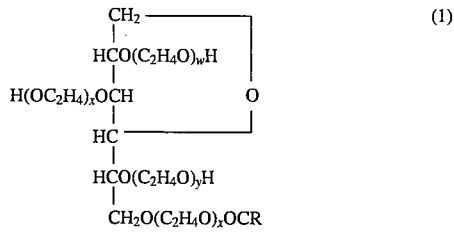

Polyoxyethylene sorbitan monoester

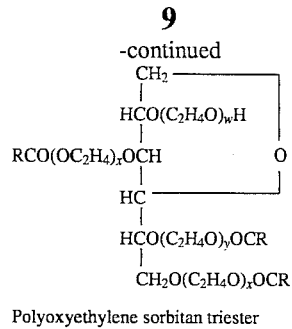

(2)

Polyoxyethylene sorbitan triester wherein the sum w+x+y+z is equal to 4, 5 or [=]20.

10. The x-ray contrast composition of claim 1 wherein said barium salt is selected from the group consisting of barium sulfate, barium hexaboride, barium chromite, barium fluogallate, barium tri-orthophosphate, barium metasilicate, barium titanate, barium zirconate and zirconium oxide.

11. The method of carrying out x-ray examination of the gastrointestinal tract of a patient, said method comprises the oral or rectal administration to the patent an x-ray contrast formulation comprising:
(a) from about 5 to 95% w/v of a barium salt;
(b) from 0.1 to 10% w/v of a cellulose derivative comprising microcrystalline cellulose;
(c) from 0.1 to 55% w/v of an oily vehicle;
(d) from 0.1 to 20% w/v of a surfactant selected from the group consisting of nonionic, anionic, cationic and zwitterionic surfactants;
(e) from 0.001 to 15% w/v of a viscosity modifying excipient;
(f) water to make 100% by volume, and then
(g) preforming an x-ray examination of the patient.

12. The x-ray contrast composition of claim 1, wherein the cellulose derivative further comprises at least one of the group consisting of methylcellulose, carboxymethylcellulose, sodium carboxymethylcellulose, hydroxyethyl methylcellulose, and hydroxypropyl methylcellulose.

13. The method according to claim 11, wherein the cellulose derivative further comprises at least one of the group consisting of methylcellulose, carboxymethylcellulose, sodium carboxymethylcellulose, hydroxyethyl methylcellulose, and hydroxypropyl methylcellulose.

14. The x-ray contrast composition according to claim 8, wherein the alkyl chain is selected from the group consisting of lauryl (dodecyl), myristyl (tetradecyl), cetyl (hexadecyl) and stearyl (octadecyl).

15. The method according to claim 11 wherein the microcrystalline cellulose has an average particle size of from 0.01 to 100 microns.

16. The method according to claim 15 wherein the cellulose derivative comprises about 89 parts microcrystalline cellulose and about 11 parts of sodium carboxymethylcellulose.

* * * * *